United States Patent [19]
Husted et al.

[11] Patent Number: 5,919,203
[45] Date of Patent: Jul. 6, 1999

[54] POWERED SURGICAL TOOL

[75] Inventors: Royce H. Husted, R.R. 4, Box 550, Forest, Va. 24551; Joel P. Husted, Forest, Va.

[73] Assignee: Royce H. Husted, Forest, Va.

[21] Appl. No.: 09/010,312

[22] Filed: Jan. 21, 1998

[51] Int. Cl.[6] .................................................... A61B 17/14
[52] U.S. Cl. ...................... 606/180; 606/176; 606/177; 606/178; 606/159
[58] Field of Search ........................... 606/180, 82, 176, 606/161, 159, 177, 178

[56] References Cited

U.S. PATENT DOCUMENTS

| 1,417,669 | 5/1922 | Langworthy | 606/180 |
|---|---|---|---|
| 1,719,557 | 7/1929 | McGrath | 606/180 |
| 2,179,250 | 11/1939 | D'amato | 606/180 |
| 3,126,889 | 3/1964 | Blumenfeld | 606/180 |
| 5,059,203 | 10/1991 | Husted | 606/159 |

Primary Examiner—Michael Buiz
Assistant Examiner—Tan-uyen T. Ho
Attorney, Agent, or Firm—Nicholas A. Camasto

[57] ABSTRACT

A powered surgical tool includes a battery-operated motor that has an eccentrically mounted drive wheel for engaging a longitudinally movable drive wire that operates to incrementally rotate a ratchet wheel. A work wheel in the form of a cutting blade or a grinding wheel is mounted for rotational movement with the ratchet wheel at the distal end of the surgical tool. In another version, the cutting blade has a periphery of cutting teeth, which are driven directly by the longitudinally movable drive wire. A grinding wheel version discloses two grinding wheels that are incrementally driven in opposite angular directions by a pair of longitudinally movable drive wires.

20 Claims, 3 Drawing Sheets

POWERED SURGICAL TOOL

BACKGROUND OF THE INVENTION AND PRIOR ART

This invention relates generally to surgical tools and specifically to a novel surgical tool that includes a powered rotary work wheel.

Conventional surgical tools, such as scalpels, have been miniaturized to enable a surgeon to perform minute incisions, often in closely confined areas. A major drawback of such cutting tools is that the surgeon must supply the required cutting action by using a reciprocal sawing or slicing motion. Consequently, even miniature tools are restricted to exposed areas of the body to which the surgeon has access or to areas that have been exposed by major surgery. Miniature scissors are frequently used in confined areas because their action traps the tissue as it is being snipped. However, they are difficult to control and leave a jagged incision due to the multiple cuttings required.

A surgical cutting tool that is powered by a remote motor means, and which therefore removes the necessity for the surgeon to provide the cutting action, is described in U.S. Pat. No. 5,059,203, issued Oct. 22, 1991 to Royce H. Husted. All the surgeon need do is guide the tool since it is powered remotely. The drive system of the patented tool uses a monofilament line for driving a work wheel to which a rotary cutting blade is affixed. The present invention incorporates an inproved drive system for powered surgical tools.

OBJECTS OF THE INVENTION

A principal object of the invention is to provide a novel powered surgical tool;

Another object of the invention is to provide a self-contained powered surgical tool that is economical to manufacture and simple to use;

A further object of the invention is to provide a powered surgical tool that has a simple drive system.

Yet another object of the invention is to provide a single use disposable powered surgical tool.

BRIEF DESCRIPTION OF THE DRAWINGS

These and other objects and advantages of the invention will be apparent upon reading the following description in conjunction with the drawings in which.

DESCRIPTION OF THE PREFERRED EMBODIMENT

The powered surgical tool of the invention achieves a very high degree of cutting efficiency due to its rotating circular blade that operates in a manner similar to a meat-slicing machine. The provision of a rotating blade results in a clean, accurate cut. This is because the surgeon need not provide a "slicing action", which invariably has the undesirable result of cutting in front of and beyond the desired area and also results in multiple cuts. The powered aspect of the inventive tool also makes the surgeon more efficient in his work. The tool of the invention is eminently suited to laproscopic surgery in which a series of holes are made with a trocar by literally punching through tissue. Due to its smooth clean slicing action, wound healing is enhanced in surgical procedures using the inventive tool. Also, because of its high cutting efficiency, the need for clamping soft tissue with a second tool is obviated.

Figure 8:
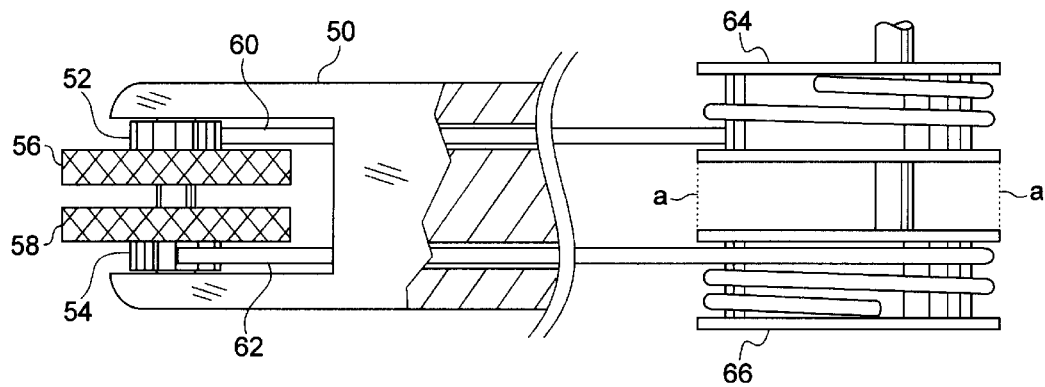
FIG. 8 illustrates a version of the surgical tool equipped with a pair of grinding wheels arranged to be rotated in opposite directions.

The preferred embodiment of the surgical tool of the invention incrementally rotates a work wheel (cutter) by the action of a rigid drive wire and a ratchet wheel. An eccentric drive wheel mounted on the shaft of a small battery-operated motor reciprocates the drive wire (in a hand-held version of the invention). The hand-held unit is preferably constructed of molded plastic with the rotating work wheel being mounted at its tip or distal end. The battery, motor and eccentric drive wheel are housed at the rear or proximal end of the powered surgical cutter and a dome type ON/OFF switch is installed in the body of the tool to permit the surgeon to control its operation. It will be appreciated that the work wheel may be sized to match the needs of various surgical specialties. The cutting blades, for example, may be as small as two millimeters in diameter. Grinding type work wheels are also contemplated, with the depiction in FIG. 8 illustrating a particularly advantageous arrangement of two grinding wheels that are rotated in opposite directions for highly efficient operation. Versions of the invention especially useful with a catheter are disclosed in FIGS. 9, 10 and 11.

Figure 1:
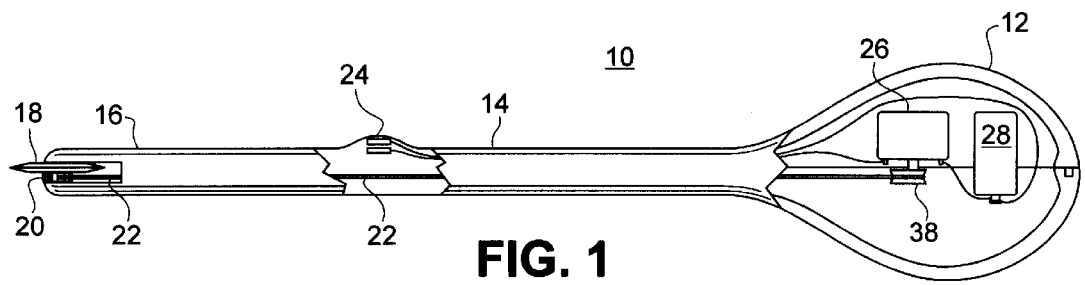
FIG. 1 is a partially cut away top view of the powered surgical tool of the invention.
Figure 2:
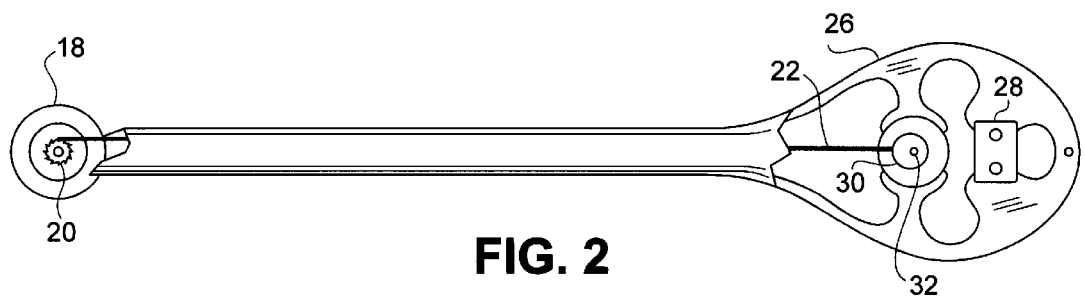
FIG. 2 is a partially cut away side view of the surgical tool.

Referring to FIGS. 1 and 2, the general configuration of a hand-held version of a power surgical tool 10, constructed in accordance with the invention, is shown. A contoured proximal end 12 is enlarged to accommodate a small motor 26 and a battery 28. A slender middle section 14 terminates in a distal end 16 that contains a work wheel 18 that is driven by means of a ratchet wheel 20. An eccentrically mounted drive wheel 30 on motor 26 reciprocates a drive wire 22 that incrementally rotates ratchet wheel 20. A small dome type switch 24 is secured in middle section 14 where it may be conveniently operated by suitable pressure applied by the surgeon. As illustrated, the housing for surgical tool 10 may be molded in two "snap together" halves with portions for securing motor 26, battery 28 and switch 24 without the need for screws or the like. A suitable guide slot may be provided for rigid drive wire 22, which may be a type of "music wire".

Figure 3:
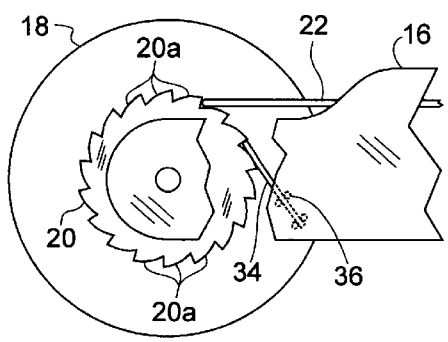
FIG. 3 is an enlarged partial view of the work wheel and drive mechanism of the surgical tool.

FIG. 3 shows how the teeth 20a of ratchet wheel 20 are engaged and driven by the end of rigid drive wire 22. An optional anti return spring 34 is shown secured between sets of molded plastic protrusions 36. It will be appreciated that other configurations are envisioned and that the depiction of a particular form of the elements is illustrative only, the invention residing in the incremental rotation of the cutting or work wheel. The overall configuration of the powered surgical tool should provide a balanced feel and be relatively lightweight to promote accuracy in use and to minimize fatigue of the user.

Figure 4:
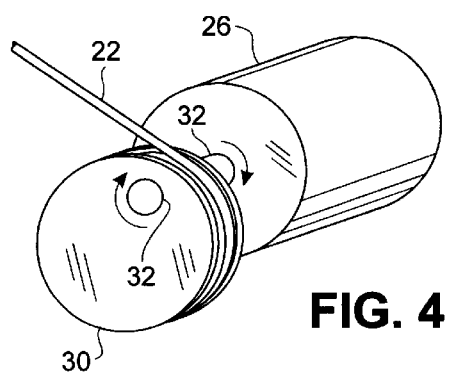
FIG. 4 is a perspective illustrating the eccentric drive wheel and motor.
Figure 5:
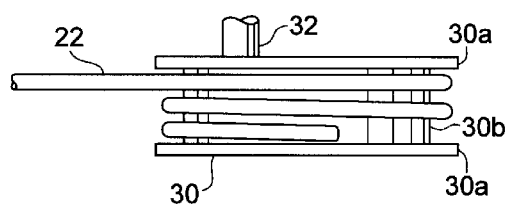
FIG. 5 illustrates engagement of the drive wire and the drive wheel.

FIGS. 4 and 5 indicate in more detail the arrangement of the eccentrically mounted drive wheel 30 and the manner of attachment of drive wire 22 thereto. In FIG. 5, drive wheel 30 includes a pair of outer portions 30a and a center portion 30b. A loop formed in the end of drive wire 22 encircles center portion 30b in a relatively loose fit so that drive wheel 30 may be freely rotated therein. As the eccentrically mounted drive wheel is rotated, a lateral translation of the drive wire takes place. This lateral translation results in a reciprocating action of the (confined) drive wire so that ratchet wheel 20 is rotated incrementally with each revolution of the drive wheel.

Figure 6:
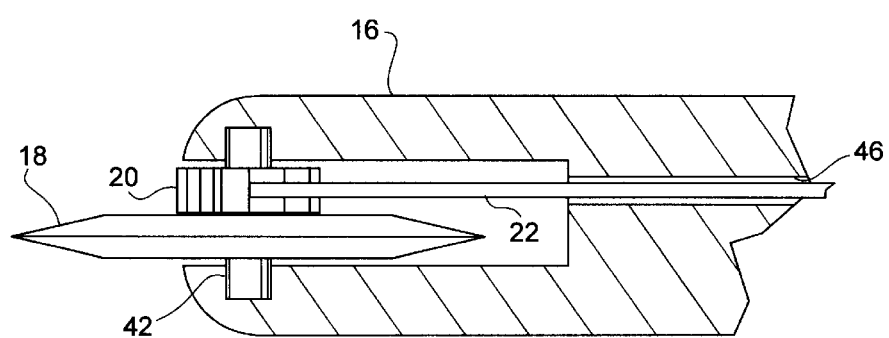
FIG. 6 is an enlarged cross section of the end of the surgical tool illustrating a practical mounting of the work wheel.

FIG. 6 illustrates one method of rotatably mounting the work wheel 18 at distal end 16 of the surgical tool. A shaft 42 is secured in the opposite walls of a U-shaped cut out portion of the distal end 16. Ratchet wheel 20 is rotatably mounted on shaft 42 and work wheel 18 is secured to ratchet wheel 20. A channel 46 is formed in the walls of the body of the surgical tool to loosely captivate drive wire 22, which undergoes slight lateral movement when driving ratchet wheel 20. It will be appreciated that the housing is preferably formed in two halves with suitable well-known mating connecting elements (not shown), which may conveniently be assembled by snapping the two halves together.

Figure 7:
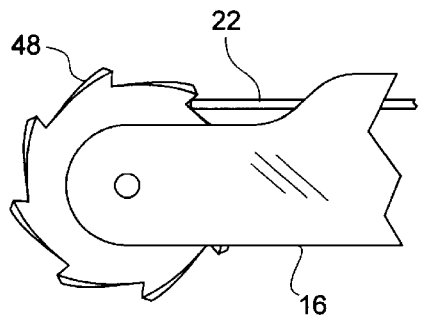

In FIG. 7, a version of the work wheel 48 is shown that eliminates the need for a separate ratchet wheel. In this embodiment, the periphery of the work wheel is in the form of cutting teeth 48a, similar to the arrangement of a saw blade, and the teeth are driven directly by drive wire 22. This configuration is especially in the construction of miniaturized cutting tools.

FIG. 8 shows a grinding wheel version of the power surgical tool. A pair of grinding wheels 56 and 58 is mounted for rotation with a corresponding pair of ratchet wheels 52 and 54, respectively. A pair of drive wires 60 and 62 cooperate with a pair of drive wheels 64 and 66 for incrementally rotating ratchet wheels 52 and 54, respectively, in opposite directions. It should be apparent that the ratchet teeth on the ratchet wheels are reversed so that drive wire 60 engages the lower portion of ratchet wheel 52 and drive wire 62 engages the upper portion of ratchet wheel 54. It will also be appreciated that a single eccentrically mounted drive wheel may be used, as indicated by the dotted lines.

Figure 9:
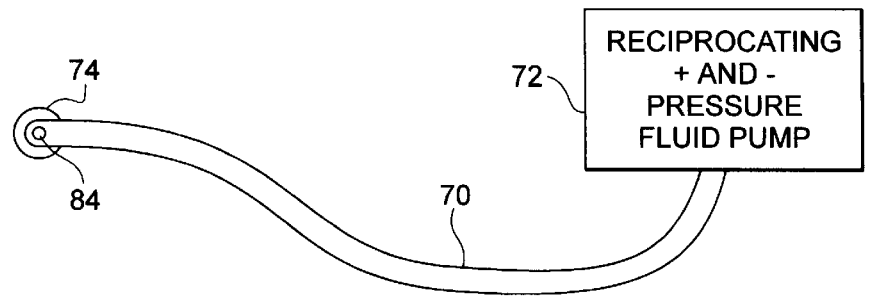
FIG. 9 illustrates a fluid driven catheter version of the invention.
Figure 10:
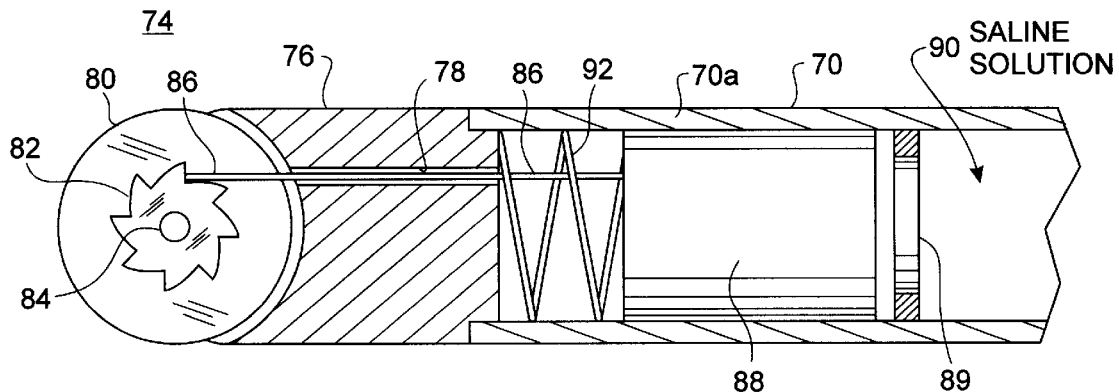
FIG. 10 shows details of the fluid piston drive mechanism.

The versions of the invention disclosed in FIGS. 9 and 10 utilize a fluid drive system for imparting incremental angular rotational movement to the work wheel. To this end a small diameter sealed tube 70 couples a reciprocating positive and negative pressure fluid pump 72 to a work wheel means 74. The work wheel means is mounted on an axle 84 and is similar to the work wheel means shown in FIGS. 1–3 and 6. A work wheel 80 and an attached ratchet wheel 82 are rotatably mounted on axle 84 that is secured in a small rigid end piece 76 that is secured to the distal end of tube 70. A rigid drive wire 86 engages ratchet wheel 82 and is driven in a reciprocating manner by a fluid piston 88 that is slidably movable in the end portion 70a of tube 70. A guide passage 78 is formed in end piece 76 to permit passage of drive wire 86. Tube 70 may be filled with a saline solution 90 or other benign fluid. Pump 72 is of well-known construction with suitable provisions for assuring that no air enters tube 70 during operation. The tube 70 may be sufficiently small in diameter to permit use of the surgical tool in many types of vascular surgery. While the positive and negative pressures developed in the tube are believed to be sufficient to effectively reciprocate fluid piston 88, a small return spring 92 has been included between the rear face of end piece 76 and the front of fluid piston 88. A stop bushing 89 is fixed in position to limit the return travel of piston 88.

Figure 11:
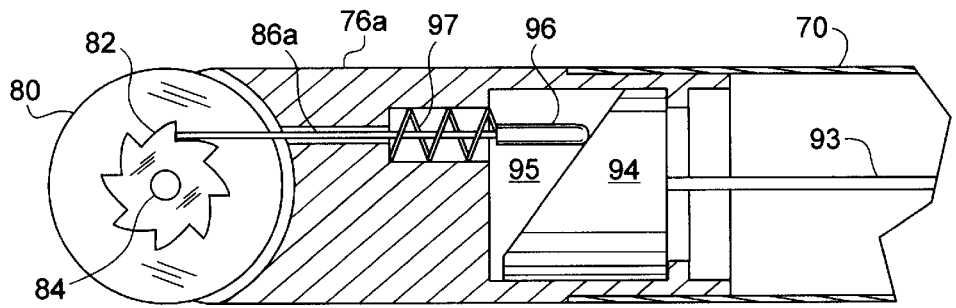
FIG. 11 illustrates another version of the invention that uses a rotary wire driven cam plate.

The version of the invention shown in FIG 11 uses a shaft 93 to rotate a cam 94 to reciprocate a push rod 96 that causes incremental rotation of a work wheel 80 at the distal end 70a of a catheter 70. Shaft 93, which is flexible, is rotatably driven by suitable motor means (not shown) to rotate cam 94 that is confined to rotary movement in a chamber 95 formed in end piece 76a. Push rod 96 is coupled to a rigid drive wire 86a that engages the teeth of a ratchet wheel 82 that is coupled to work wheel 80. A spring 97 biases push rod 96 against the face of cam 94. As cam 94 rotates, push rod 96 undergoes reciprocating transverse motion which causes drive wire 86a to incrementally advance ratchet wheel 82 (and incrementally rotate work wheel 80).

What has been described is a novel powered surgical tool that utilizes a reciprocating drive arrangement for rotating a work wheel. The invention is suitable for use in hand-held scalpels used in conventional surgery as well as in intervascular and laproscopic surgery. It is recognized that numerous modifications in the described embodiments of the invention will occur to those skilled in the art without departing from its true spirit and scope. The invention is to be limited only as defined in the claims.

What is claimed is:

1. A powered miniature tool comprising:

work wheel means having an axis of rotation;

a housing having a proximal end and a distal end;

means in said housing for supporting said work wheel means for rotation about said axis;

a reciprocally movable element in said housing for imparting incremental angular undirectional rotational movement to said work wheel means; and motor means coupled to said reciprocally movable element adjacent said proximal end of said housing.

2. The tool of claim 1, wherein said work wheel means comprises a circular work wheel having an axle corresponding to said axis, and wherein said work wheel has a toothed periphery that is engaged by said reciprocally movable element.

3. The tool of claim 1, wherein said reciprocally movable element comprises a length of music wire.

4. The tool of claim 1, wherein said motor means further includes:

an eccentrically mounted drive wheel that engages a looped portion of said reciprocally movable element.

5. The tool of claim 1, wherein said work wheel means includes a work wheel defining a cutting edge and further including a ratchet wheel coupled to said work wheel, said ratchet wheel being engageable with said reciprocally movable element.

6. The tool of claim 1, further including:

means for converting rotational motion to longitudinal motion coupled between said motor means and said reciprocally movable element.

7. The tool of claim 6, wherein said rotational motion converting means comprises:

A flexible shaft coupled to said motor means;

a rotatable cam driven from said flexible shaft; and a push rod engaging said cam and said reciprocally movable element.

8. The tool of claim 1, wherein said housing comprises a sealed tube and wherein:

said motor means comprises a fluid pump developing positive and negative pressure; and a fluid piston mounted in said distal end for reciprocating said reciprocally movable element in response to fluid pressures in said tube.

9. The tool of claim 8, wherein said reciprocally movable element comprises a length of music wire.

10. The tool of claim 8, wherein said work wheel defines a cutting edge and further including a ratchet wheel coupled to said work wheel, said ratchet wheel being engageable with said reciprocally movable element.

11. A powered miniature tool comprising:

a circular work wheel having an axis of rotation;

a housing having a proximal end and a distal end;

means in said housing for supporting said work wheel for rotation about said axis;

a reciprocally movable element in said housing for imparting incremental unidirectional angular rotational movement to said work wheel;

motor means coupled to said reciprocally movable element adjacent said proximal end of said housing, said work wheel having an axle corresponding to said axis; and an eccentrically mounted drive wheel in said motor means that engages a looped portion of said reciprocally movable element.

12. The tool of claim 11, further comprising:

a second circular work wheel;

a second reciprocally movable element for imparting incremental unidirectional angular rotational movement to said second work wheel; and said second reciprocally movable element driving said second work wheel in an opposite unidirectional angular direction.

13. A method of operating a powered surgical cutter comprising:

providing a work wheel having a cutting edge;

supporting the work wheel for rotational movement at the distal end of a housing;

providing a reciprocally movable element coupled to a motor means located in the proximal end of the housing and driving the work wheel in an incremental unidirectional angular rotational manner from the reciprocally movable element.

14. The method of claim 13, wherein a ratchet wheel is coupled to the work wheel and further comprising:

driving the ratchet wheel with the reciprocally movable element.

15. The method of claim 13, wherein the housing comprises a sealed, fluid filled tube and further comprising:

providing a positive and negative pressure fluid pump at one end of the sealed tube and a reciprocally movable fluid piston at the other end of the sealed tube; and coupling the fluid piston to the work wheel.

16. The method of claim 15, further comprising: applying force from the fluid piston to a ratchet wheel coupled to the work wheel.

17. The method of claim 13, further comprising:

sequentially engaging the serrated cutting edge of the work wheel with a reciprocally movable element that is coupled for reciprocating motion to the motor means.

18. The method of claim 13, wherein two work wheels are provided that are driven in opposite incremental undirectional angular rotations from the motor means.

19. The method of claim 13, further comprising:

providing a cam;

providing a push rod that engages the work wheel; and driving the cam with a flexible shaft coupled to the motor means for converting rotational motion of the motor means to reciprocal motion of the push rod.

20. The method of claim 19, further including biasing the push rod against the face of the cam.

* * * * *